(12) United States Patent
Yoshioka et al.

(10) Patent No.: US 10,547,012 B2
(45) Date of Patent: Jan. 28, 2020

(54) PHOTOELECTRIC CONVERSION ELEMENT, IMAGING ELEMENT, OPTICAL SENSOR, AND COMPOUND

(71) Applicant: FUJIFILM Corporation, Tokyo (JP)

(72) Inventors: Tomoaki Yoshioka, Kanagawa (JP); Naoyuki Hanaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 140 days.

(21) Appl. No.: 15/871,873

(22) Filed: Jan. 15, 2018

(65) Prior Publication Data

US 2018/0159039 A1    Jun. 7, 2018

Related U.S. Application Data

(63) Continuation of application No. PCT/JP2016/071590, filed on Jul. 22, 2016.

(30) Foreign Application Priority Data

Jul. 30, 2015    (JP) .................... 2015-151022

(51) Int. Cl.
*H01L 51/00* (2006.01)
*C07F 5/02* (2006.01)
(Continued)

(52) U.S. Cl.
CPC .......... *H01L 51/008* (2013.01); *C07F 5/022* (2013.01); *H01L 27/148* (2013.01); (Continued)

(58) Field of Classification Search
CPC .................... H01L 51/008; C07F 5/022
See application file for complete search history.

(56) References Cited

U.S. PATENT DOCUMENTS 8,569,747 B2 * 10/2013 Yoshinaga .......... H01L 51/0056
257/40
10,150,911 B2 * 12/2018 Lee ...................... C07F 5/02
(Continued)

FOREIGN PATENT DOCUMENTS

CN    102993763    3/2013
JP    2008-109097    5/2008
(Continued)

OTHER PUBLICATIONS

Machine translation of JP 2008-109097 A. (Year: 2008).*
(Continued)

*Primary Examiner* — Vu A Nguyen
(74) *Attorney, Agent, or Firm* — JCIPRNET

(57) ABSTRACT

The present invention provides a photoelectric conversion element exhibiting excellent low dark current characteristics and heat resistance, an imaging element and an optical sensor which include the photoelectric conversion element, and a compound. The photoelectric conversion element of the present invention is a photoelectric conversion element photoelectric conversion element having a conductive film, a photoelectric conversion film, and a transparent conductive film in this order, in which the photoelectric conversion film contains a compound represented by General Formula (1) and an organic n-type compound.

(Continued)

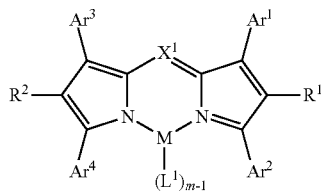

General Formula (1)

19 Claims, 2 Drawing Sheets

(51) Int. Cl.
H01L 27/146 (2006.01)
H01L 27/30 (2006.01)
H01L 27/148 (2006.01)
H01L 51/42 (2006.01)

(52) U.S. Cl.
CPC .. H01L 27/14643 (2013.01); H01L 27/14667 (2013.01); H01L 27/307 (2013.01); H01L 51/4253 (2013.01)

(56) References Cited

U.S. PATENT DOCUMENTS

2011/0303903 A1 12/2011 Yoshinaga et al.
2014/0231781 A1 8/2014 Imai

FOREIGN PATENT DOCUMENTS

| JP | 2008109097 A | * | 5/2008 |
| JP | 2010-040735 | | 2/2010 |
| JP | 2013-118365 | | 6/2013 |
| JP | 5907289 | | 4/2016 |

OTHER PUBLICATIONS

SciFinder Searches (Year: 2019).*
SciFinder Search (Nov. 5, 2019).*
Leem et al., "Low dark current small molecule organic photodetectors with selective response to green light", Applied Physics Letters, Jul. 24, 2013, pp. 043305-1-043305-5.
Leblebici et al., "Near-Infrared Azadipyrromethenes as Electron Donor for Efficient Planar Heterojunction Organic Solar Cells", ACS Applied Materials & Interfaces, Oct. 27, 2011, pp. 4469-4474.
Mueller et al., "Organic solar cells based on a novel infrared absorbing aza-bodipy dye", Solar Energy Materials & Solar Cells, Jan. 10, 2012, pp. 176-181.
Jiang et al., "A near-infrared dye based on BODIPY for tracking morphology changes in mitochondria", Chemical Communications, 2013, pp. 10620-10622.
"International Search Report (Form PCT/ISA/210) of PCT/JP2016/071590", with English translation thereof, dated Sep. 6, 2016, pp. 1-4.
"Written Opinion (Form PCT/ISA/237)", dated Sep. 6, 2016, with English translation thereof, pp. 1-15.
"Office Action of Japan Counterpart Application," with English translation thereof, dated Jan. 22, 2019, p. 1-p. 6.

* cited by examiner

PHOTOELECTRIC CONVERSION ELEMENT, IMAGING ELEMENT, OPTICAL SENSOR, AND COMPOUND

CROSS-REFERENCE TO RELATED APPLICATIONS

This application is a Continuation of PCT International Application No. PCT/JP2016/071590 filed on Jul. 22, 2016, which claims priority under 35 U.S.C. § 119(a) to Japanese Patent Application No. 2015-151022 filed on Jul. 30, 2015. The above application is hereby expressly incorporated by reference, in its entirety, into the present application.

BACKGROUND OF THE INVENTION

1. Field of the Invention

The present invention relates to a photoelectric conversion element, an imaging element, an optical sensor, and a compound.

2. Description of the Related Art

An optical sensor in the related art is an element in which a photodiode (PD) is formed in a semiconductor substrate of silicon (Si) or the like. A planar solid-state imaging element in which PD's are two-dimensionally arranged and a signal charge generated in each PD is read out by a circuit is widely used as a solid-state imaging element.

In order to realize a color solid-state imaging element, a structure in which color filters transmitting light of a specific wavelength are arranged on a light incident surface side of the planar solid-state imaging element is generally used. Currently, single plate type solid-state imaging element which is widely used in digital cameras and in which color filters transmitting blue (B) light, green (G) light, and red (R) light are regularly arranged on each of the PD's that have been two-dimensionally arranged is well-known. However, in the single plate type solid-state imaging element, light which has not been transmitted through the color filters is not used, and therefore, light utilization efficiency is poor.

In order to solve these disadvantages, in recent years, development of an element having a structure in which an organic photoelectric conversion film is formed on a substrate for reading out a signal has progressed. Various examinations have been conducted on a photoelectric conversion element in which such an organic photoelectric conversion film is used, for the purpose, for example, of controlling a dark current (for example, Applied Physics Letters 2013, 103, 043305).

SUMMARY OF THE INVENTION

In recent years, further improvement is also required regarding various characteristics required for photoelectric conversion elements used in an imaging element, an optical sensor, and the like in response to demands for improvement in performance of the imaging element, the optical sensor, and the like.

For example, further reduction in dark current is required.

In addition, in the photoelectric conversion element, it is necessary to maintain the same level of the excellent characteristics as that before predetermined heat treatment even after the heat treatment is performed and it is particularly necessary for a dark current not to increase even after the heat treatment. That is, it is necessary to improve heat resistance of the photoelectric conversion element.

The present inventors have manufactured the photoelectric conversion element disclosed in Applied Physics Letters 2013, 103, 043305 and examined the characteristics. As a result, the dark current characteristics and the heat resistance (dark current characteristics after the heat treatment) of the obtained photoelectric conversion element do not necessarily reach a level recently required, and therefore, it was found that improvement is further required.

The present invention has been made in consideration of the above-described circumstances, and an object of the present invention is to provide a photoelectric conversion element exhibiting excellent low dark current characteristics and heat resistance.

In addition, another object of the present invention is to provide an imaging element and an optical sensor which include a photoelectric conversion element. Still another object of the present invention is to provide a compound applied to the above-described photoelectric conversion element.

The present inventors have conducted extensive studies on the above-described problems. As a result, they have found that it is possible to solve the above-described problems using a pyrromethene compound having a predetermined structure and a photoelectric conversion film containing an organic n-type compound, and have completed the present invention.

That is, the above-described problems can be solved by means shown below.

(1) A photoelectric conversion element having a conductive film, a photoelectric conversion film, and a transparent conductive film in this order, in which the photoelectric conversion film contains a compound represented by General Formula (1) and an organic n-type compound to be described below.

(2) The photoelectric conversion element according to (1), in which the compound represented by General Formula (1) is a compound represented by General Formula (2) to be described below.

(3) The photoelectric conversion element according to (2), in which $R^4$ in General Formula (2) is a heteroaryl group.

(4) The photoelectric conversion element according to (3), in which a hetero atom contained in the heteroaryl group is a sulfur atom.

(5) The photoelectric conversion element according to any one of (2) to (4), in which $L^2$ and $L^3$ in General Formula (2) are both fluorine atoms.

(6) The photoelectric conversion element according to any one of (2) to (5), in which $Ar^1$ to $Ar^4$ in General Formula (2) are all aryl groups.

(7) The photoelectric conversion element according to any one of (1) to (6), in which the molecular weight of the organic n-type compound is 300 to 900.

(8) The photoelectric conversion element according to any one of (1) to (7), in which the photoelectric conversion film has a bulk hetero structure formed of the compound represented by General Formula (1) and the organic n-type compound.

(9) An optical sensor comprising: the photoelectric conversion element according to any one of (1) to (8).

(10) An imaging element comprising: the photoelectric conversion element according to any one of (1) to (8).

(11) A compound represented by General Formula (3) to be described below.

According to the present invention, it is possible to provide a photoelectric conversion element exhibiting excellent low dark current characteristics and heat resistance.

In addition, according to the present invention, it is also possible to provide an imaging element and an optical sensor which include the photoelectric conversion element. Furthermore, according to the present invention, it is also possible to provide a compound applied to the above-described photoelectric conversion element.

DESCRIPTION OF THE PREFERRED EMBODIMENTS

Hereinafter, suitable embodiments of the photoelectric conversion element of the present invention will be described.

In the present specification, a substituent or the like for which it is not specified whether the group is substituted or unsubstituted means that the group may further have a substituent W to be described below within the scope not impairing an objective effect. For example, the expression "alkyl group" corresponds to an alkyl group which may have a substituent W.

In addition, in the present specification, the numerical range represented by "to" means a range including numerical values denoted before and after "to" as a lower limit value and an upper limit value.

An example of features compared with the prior art of the present invention is that a compound represented by General Formula (1) having a predetermined structure (hereinafter, also simply referred to as a "specific pyrromethene compound"). The detailed reason why a desired effect can be obtained using the specific pyrromethene compound is unknown, but is estimated as follows. First, the present inventors have conducted tests, and as a result, they have found that a dark current tends to increase as crystallization of the compound progresses in a photoelectric conversion film (particularly a photoelectric conversion film having a bulk hetero structure). As a result of further examinations based on such a finding, it has been confirmed that the specific pyrromethene compound is hardly crystallized due to the three-dimensional structure thereof, and as a result, a dark current decreases. In addition, even in a case where heat treatment is performed on a photoelectric conversion element, it is considered that increase of a dark current is suppressed due to the difficulty in crystallization of the specific pyrromethene compound.

Figure 1A:
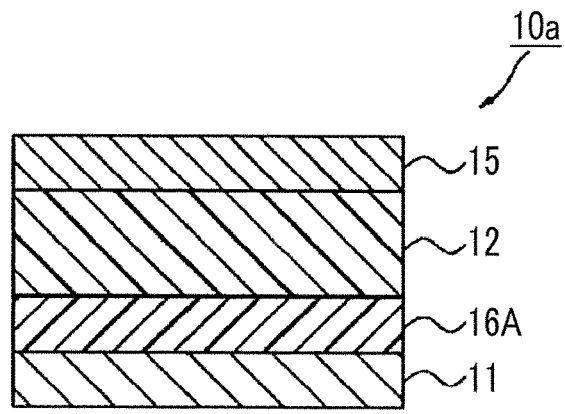
FIG. 1A is a schematic cross-sectional view showing a configuration example of a photoelectric conversion element.

Hereinafter, suitable embodiments of the photoelectric conversion element of the present invention will be described with reference to the drawings. Schematic cross-sectional views of an embodiment of a photoelectric conversion element of the present invention are shown in FIGS. 1A and 1B.

A photoelectric conversion element 10a shown in FIG. 1A has a configuration in which a conductive film (hereinafter, also referred to as a lower electrode) 11 functioning as the lower electrode, an electron blocking film 16A formed on the lower electrode 11, a photoelectric conversion film 12 which contains a compound represented by General Formula (1) to be described below and an organic n-type compound and is formed on the electron blocking film 16A, and a transparent conductive film (hereinafter, also referred to as an upper electrode) 15 functioning as the upper electrode are laminated in this order.

Figure 1B:
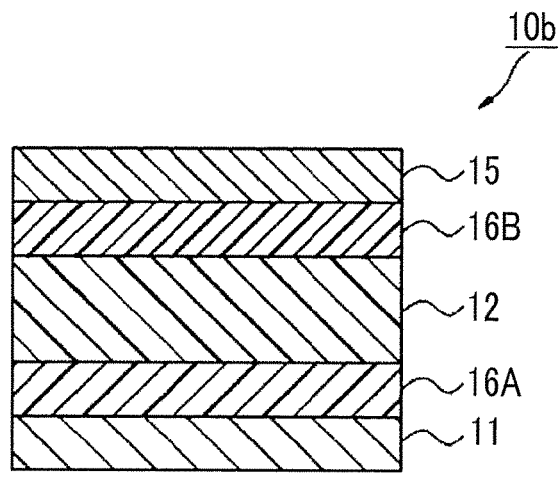
FIG. 1B is a schematic cross-sectional view showing a configuration example of a photoelectric conversion element.

A configuration example of another photoelectric conversion element is shown in FIG. 1B. A photoelectric conversion element 10b shown in FIG. 1B has a configuration in which an electron blocking film 16A, a photoelectric conversion film 12, a hole blocking film 16B, and an upper electrode 15 are laminated on a lower electrode 11 in this order. The lamination order of the electron blocking film 16A, the photoelectric conversion film 12, and the hole blocking film 16B in FIGS. 1A and 1B may be reversed in accordance with the application and characteristics. For example, the positions of the electron blocking film 16A and the photoelectric conversion film 12 may be reversed.

In the configuration of the photoelectric conversion element 10a (10b), light is preferably incident on the photoelectric conversion film 12 through the transparent conductive film 15.

In addition, in a case of using the photoelectric conversion element 10a (10b), a voltage can be applied. In this case, it is preferable that the conductive film 11 and the transparent conductive film 15 form a pair of electrodes and a voltage of $1 \times 10^{-5}$ to $1 \times 10^{7}$ V/cm is applied between this pair of electrodes. From the viewpoints of performance and power consumption, a voltage of $1 \times 10^{-4}$ to $1 \times 10^{7}$ V/cm is preferable and a voltage of $1 \times 10^{-3}$ to $5 \times 10^{6}$ V/cm is more preferable.

As the voltage application method, application of a voltage is preferably performed such that the electron blocking film 16A side in FIGS. 1A and 1B becomes a cathode and the photoelectric conversion film 12 side becomes an anode. It is possible to perform application of a voltage through the same method in cases where the photoelectric conversion element 10a (10b) is used as an optical sensor or is incorporated into an imaging element.

As will be described in detail below, the photoelectric conversion element 10a (10b) can be suitably applied to applications of the imaging element and the optical sensor.

Figure 2:
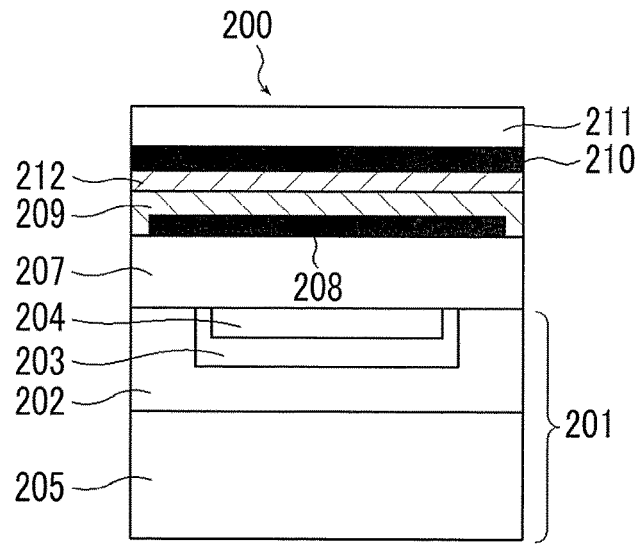
FIG. 2 is a schematic cross-sectional view of one pixel of a hybrid type photoelectric conversion element.

In addition, a schematic cross-sectional view of another embodiment of a photoelectric conversion element of the present invention is shown in FIG. 2.

A photoelectric conversion element 200 shown in FIG. 2 represents a hybrid type photoelectric conversion element including an organic photoelectric conversion film 209 and an inorganic photoelectric conversion film 201. The organic photoelectric conversion film 209 includes a compound represented by General Formula (1) and an organic n-type compound to be described below.

The inorganic photoelectric conversion film 201 has an n-type well 202, a p-type well 203, and an n-type well 204 on a p-type silicon substrate 205.

Blue light is photoelectrically converted (B pixel) at a p-n junction formed between the p-type well 203 and the n-type well 204 and red light is photoelectrically converted (R pixel) at a p-n junction formed between the p-type well 203 and the n-type well 202. Note that the conduction types of the n-type well 202, the p-type well 203, and the n-type well 204 are not limited thereto, and may be opposite conduction types.

Furthermore, a transparent insulating layer 207 is formed on the inorganic photoelectric conversion film 201.

A transparent pixel electrode 208 divided for each pixel is formed on the insulating layer 207, the organic photoelectric conversion film 209 which absorbs green light and performs photoelectric conversion is formed on the pixel electrode in a single layer configuration commonly for each pixel, an electron blocking film 212 is formed on the organic photoelectric conversion film in a single layer configuration commonly for each pixel, a transparent common electrode 210 with a single layer configuration as well is formed on the electron blocking film, and a transparent protective film 211 is formed on the uppermost layer. The lamination order of the electron blocking film 212 and the organic photoelectric conversion film 209 may be reversed from that in FIG. 2, and the common electrode 210 may be divided for each pixel.

The organic photoelectric conversion film 209 constitutes a G pixel for detecting green light.

The pixel electrode 208 is the same as the lower electrode 11 of the photoelectric conversion element 10a shown in FIG. 1A. The common electrode 210 is the same as the upper electrode 15 of the photoelectric conversion element 10a shown in FIG. 1A.

In a case where light from a subject is incident on the photoelectric conversion element 200, green light in the incident light is absorbed by the organic photoelectric conversion film 209 to generate optical charges. The optical charges flow into and accumulate in a green signal charge accumulation region not shown in the drawing from the pixel electrode 208.

The mixed light of the blue light and the red light transmitted through the organic photoelectric conversion film 209 enters the inorganic photoelectric conversion film 201. The blue light having a short wavelength is photoelectrically converted mainly at a shallow portion (in the vicinity of a p-n junction formed between the p-type well 203 and the n-type well 204) of a semiconductor substrate (inorganic photoelectric conversion film) 201 to generate optical charges, and a blue signal is output to the outside. The red light having a long wavelength is photoelectrically converted mainly at a deep portion (in the vicinity of a p-n junction formed between the p-type well 203 and the n-type well 202) of the semiconductor substrate (inorganic photoelectric conversion film) 201 to generate optical charges, and a red signal is output to the outside.

In a case where the photoelectric conversion element 200 is used in an imaging element, a signal readout circuit (an electric charge transfer path in a case of a charge coupled device (CCD) type or a metal-oxide-semiconductor (MOS) transistor circuit in a case of a complementary metal oxide semiconductor (CMOS) type) or a green signal charge accumulation region is formed in a surface portion of a p-type silicon substrate 205. In addition, the pixel electrode 208 is connected to the corresponding green signal charge accumulation region through vertical wiring.

Hereinafter, embodiments of each layer constituting the photoelectric conversion element of the present invention will be described in detail.

[Photoelectric Conversion Film]

(Compound Represented by General Formula (1))

The photoelectric conversion film 12 (or the organic photoelectric conversion film 209) is a film containing a compound represented by General Formula (1) as a photoelectric conversion material. By using the compound, a photoelectric conversion element which exhibits excellent low dark current characteristics and heat resistance and has a photoelectric conversion film.

Hereinafter, the compound represented by General Formula (1) will be described in detail.

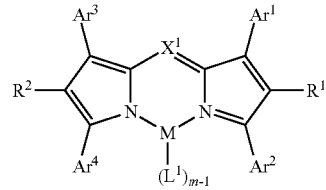

General Formula (1)

$Ar^1$ to $Ar^4$ in General Formula (1) each independently represent an aryl group or a heteroaryl group. Among them, an aryl group is preferable from a viewpoint in which at least any one of (hereinafter, also simply referred to as a "viewpoint in which the effect of the present invention is more excellent" can be obtained) a viewpoint in which dark current further increases and a viewpoint in which heat resistance is further improved.

The number of carbon atoms in the aryl group is not particularly limited, but 6 to 30 is preferable and 6 to 18 is more preferable from the viewpoint of in which the effect of the present invention is more excellent. The aryl group may have a monocyclic structure or a condensed ring structure (fused ring structure) in which two or more rings are condensed, or may have a substituent W to be described below.

Examples of the aryl group include a phenyl group, a naphthyl group, an anthryl group, a pyrenyl group, a phenanthrenyl group, a methylphenyl group, a dimethylphenyl group, a biphenyl group, and a fluorenyl group, and a phenyl group, a naphthyl group, or an anthryl group is preferable.

The number of carbon atoms in the heteroaryl group (monovalent aromatic heterocyclic group) is not particularly limited, but is preferably 3 to 30 is preferable and 3 to 18 is more preferable from the viewpoint in which the effect of the present invention is more excellent. The heteroaryl group may have a substituent W to be described below.

A hetero atom is included in the heteroaryl group in addition to a carbon atom and a hydrogen atom. Examples of the hetero atom include a nitrogen atom, a sulfur atom, an oxygen atom, a selenium atom, a tellurium atom, a phosphorus atom, a silicon atom, and a boron atom. A nitrogen atom, a sulfur atom, or an oxygen atom is preferable, and a sulfur atom is more preferable.

The number of hetero atoms contained in the heteroaryl group is not particularly limited, and is usually about 1 to 10 and preferably 1 to 4.

The number of ring members of the heteroaryl group is not particularly limited, but is preferably a 3- to 8-membered ring, more preferably a 5- to 7-membered ring, and still more preferably a 5- to 6-membered ring. The heteroaryl group may have a monocyclic structure or a condensed ring structure in which two or more rings are condensed, or may have a substituent W to be described below. In the case of the condensed ring structure, an aromatic hydrocarbon ring (for example, a benzene ring structure) which does not contain a hetero atom may be contained therein.

Examples of the heteroaryl group include a pyridyl group, a quinolyl group, an isoquinolyl group, an acridinyl group, a phenanthridinyl group, a pteridinyl group, a pyrazinyl group, a quinoxalinyl group, a pyrimidinyl group, a quinazolyl group, a pyridazinyl group, a cinnolinyl group, a phthalazinyl group, a triazinyl group, an oxazolyl group, a benzoxazolyl group, a thiazolyl group, a benzothiazolyl group, an imidazolyl group, a benzimidazolyl group, a pyrazolyl group, an indazolyl group, an isoxazolyl group, a benzisoxazolyl group, an isothiazolyl group, a benzisothiazolyl group, an oxadiazolyl group, a thiadiazolyl group, a triazolyl group, a tetrazolyl group, a furyl group, a benzofuryl group, a thienyl group, a benzothienyl group, a dibenzofuryl group, a dibenzothienyl group, a pyrrolyl group, an indolyl group, an imidazopyridinyl group, and a carbazolyl group.

$R^1$ and $R^2$ each independently represent a hydrogen atom or a substituent. Among them, both $R^1$ and $R^2$ are preferably hydrogen atoms from the viewpoint in which the effect of the present invention is more excellent.

The definition of the above-described substituent is synonymous with a substituent W to be described below. Among them, an alkyl group, an aryl group, a heteroaryl group, and the like are suitably exemplified as the substituent.

$X^1$ represents a nitrogen atom (=N—) or $CR^3$ (=$CR^3$—) and $R^3$ represents an alkyl group, an aryl group, or a heteroaryl group. Among them, $X^1$ is preferably $CR^3$ from the viewpoint in which the effect of the present invention is more excellent. In addition, an aryl group or a heteroaryl group is preferable and a heteroaryl group is more preferable as $R^3$ from the viewpoint in which the effect of the present invention is more excellent.

The definition of an aryl group and a heteroaryl group is as described above.

In a case where $R^3$ is a heteroaryl group which has a condensed ring structure including an aromatic hydrocarbon ring (for example, a benzene ring structure) which does not contain a hetero atom, a ring structure portion containing a hetero atom in $R^3$ is preferably bonded to a carbon atom (C) in a group represented by $CR^3$. In addition, in a case where $R^3$ is a heteroaryl group, it is preferable that the aromatic hydrocarbon ring which does not contain a hetero atom is not contained in the heteroaryl group from the viewpoint in which the effect of the present invention is more excellent. That is, the heteroaryl group is preferably a group formed of only a ring structure containing a hetero atom. In this case, the heteroaryl group may have a monocyclic structure or may be a group in which two or more ring structures containing a hetero atom are condensed.

The number of carbon atoms in an alkyl group is not particularly limited, but is preferably 1 to 10 and more preferably 1 to 6 from the viewpoint in which the effect of the present invention is more excellent. The alkyl group may have any of linear, branched, and cyclic structures.

Preferred examples of the alkyl group include a methyl group, an ethyl group, an n-propyl group, an i-propyl group, an n-butyl group, an n-hexyl group, and a cyclohexyl group.

M represents a kind of atom selected from the group consisting of boron (boron atom), beryllium (beryllium atom), magnesium (magnesium atom), chromium (chromium atom), iron (iron atom), nickel (nickel atom), copper (copper atom), zinc (zinc atom), and platinum (platinum atom). Among them, boron or zinc is preferable and boron is more preferable from the viewpoint in which the effect of the present invention is more excellent.

$L^1$ represents a group capable of bonding to M. Examples of the group capable of bonding to M include a halogen atom, an alkyl group, an aryl group, a heteroaryl group, an alkoxy group, an aryloxy group, an alkylthio group, an arylthio group, a cyano group, and a nitro group. Among them, a halogen atom, an alkoxy group, an aryl group, or an alkyl group is preferable and a halogen atom is more preferable from the viewpoint in which the effect of the present invention is more excellent. Examples of the halogen atom include a fluorine atom, a chlorine atom, a bromine atom, and an iodine atom, and are preferably a fluorine atom from the viewpoint in which the effect of the present invention is more excellent.

In a case where there are a plurality of $L^1$'s, the plurality of $L^1$'s may be the same as or different from each other.

m represents a valence of an atom represented by M. For example, in a case where M is a boron atom, m represents 3.

In general, 1 to 4 are preferably selected and 3 and 4 are more preferably selected as the specific numerical value of m.

SUITABLE EMBODIMENT

Examples of a suitable embodiment of the compound represented by General Formula (1) include a compound represented by General Formula (2) from the viewpoint of in which the effect of the present invention is more excellent.

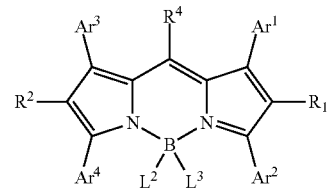

General Formula (2)

In General Formula (2), $Ar^1$ to $Ar^4$ each independently represent an aryl group or a heteroaryl group. $R^1$ and $R^2$ each independently represent a hydrogen atom or a substituent.

The definition and the suitable range of $Ar^1$ to $Ar^4$ and $R^1$ and $R^2$ are synonymous with those in the above-described General Formula (1).

$R^4$ represents an alkyl group, an aryl group, or a heteroaryl group. Among them, a heteroaryl group is preferably from the viewpoint in which the effect of the present invention is more excellent.

The definition of an alkyl group, an aryl group, and a heteroaryl group is as described above.

In addition, in a case where $R^4$ is a heteroaryl group which has a condensed ring structure including an aromatic hydrocarbon ring (for example, a benzene ring structure) which does not contain a hetero atom, a ring structure portion containing a hetero atom in $R^4$ is preferably bonded to a bond in General Formula (2). In addition, in a case where $R^4$ is a heteroaryl group, it is preferable that the aromatic hydrocarbon ring which does not contain a hetero atom is not contained in the heteroaryl group from the viewpoint in which the effect of the present invention is more excellent. That is, the heteroaryl group is preferably a group formed of only a ring structure containing a hetero atom. In this case, the heteroaryl group may have a monocyclic structure or may be a group in which two or more ring structures containing a hetero atom are condensed.

$L^2$ and $L^3$ each independently represent a type selected from the group consisting of a halogen atom, an alkyl group, an aryl group, a heteroaryl group, an alkoxy group, an aryloxy group, an alkylthio group, an arylthio group, a cyano group, and a nitro group. Among them, both of $L^2$ and $L^3$ are preferably a halogen atom, an alkoxy group, an aryl group, or an alkyl group and more preferably a halogen atom from the viewpoint in which the effect of the present invention is more excellent.

In addition, examples of the most suitable embodiment of the compound represented by General Formula (1) include a compound represented by General Formula (3) from the viewpoint in which the effect of the present invention is more excellent.

Y-Het¹  General Formula (3)

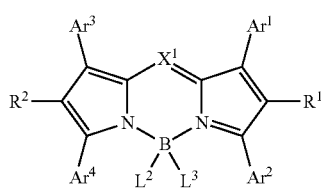

General Formula (4)

The above-described General Formula (3) is also represented by the following structural formula.

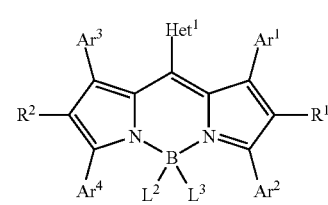

In General Formula (3), Y represents a mother nucleus represented by General Formula (4). * represents a bonding position with Het¹.

In General Formula (4), the definition and the suitable range of $Ar^1$ to $Ar^4$, $R^1$ and $R^2$, and $L^2$ and $L^3$ are synonymous with those in the above-described General Formula (2).

Het¹ represents a heteroaryl group bonded to the mother nucleus at a ring containing a hetero atom. The definition of the heteroaryl group is as described above.

As the definition of the heteroaryl group represented by the above-described Het¹, the heteroaryl group is intended to be bonded to the above-described mother nucleus in a ring portion containing a hetero atom in a case where the heteroaryl group has a condensed ring structure which includes a ring containing a hetero atom and an aromatic hydrocarbon ring (for example, a benzene ring structure) which does not contain a hetero atom. In addition, the aromatic hydrocarbon ring which does not contain a hetero atom is preferably not contained in the heteroaryl group from the viewpoint in which the effect of the present invention is more excellent. That is, the heteroaryl group is preferably a group formed of only a ring structure containing a hetero atom. In this case, the heteroaryl group may have a monocyclic structure or may be a group in which two or more ring structures containing a hetero atom are condensed.

The substituent W in the present specification will be described below.

Examples of the substituent W include a halogen atom, an alkyl group (including a cycloalkyl group, a bicycloalkyl group, and a tricycloalkyl group), an alkenyl group (including a cycloalkenyl group and a bicycloalkenyl group), an alkynyl group, an aryl group, a heterocyclic group, a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonium group, an acylamino group, an aminocarbonylamino group, an alkoxycarbonylamino group, an aryloxycarbonylamino group, a sulfamoylamino group, an alkyl- or arylsulfonylamino group, a mercapto group, an alkylthio group, an arylthio group, a heterocyclic thio group, a sulfamoyl group, a sulfo group, an alkyl- or arylsulfinyl group, an alkyl- or arylsulfonyl group, an acyl group, an aryloxycarbonyl group, an alkoxycarbonyl group, A carbamoyl group, an aryl- or heterocyclic azo group, an imide group, a phosphino group, a phosphinyl group, a phosphinyloxy group, a phosphinylamino group, a phosphono group, a silyl group, a hydrazino group, a ureido group, a boronic acid group ($—B(OH)_2$), a phosphato group ($—OPO(OH)_2$), a sulfato group ($—OSO_3H$), and other well-known substituents.

The details of the substituent W are disclosed in paragraph [0023] of JP2007-234651A.

Hereinafter, the compound represented by General Formula (1) will be exemplified.

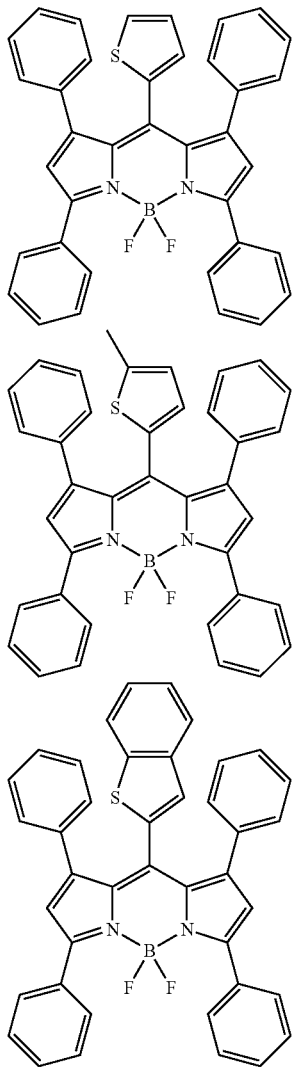

-continued
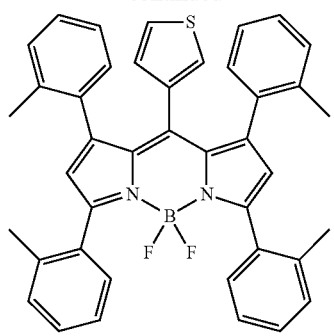
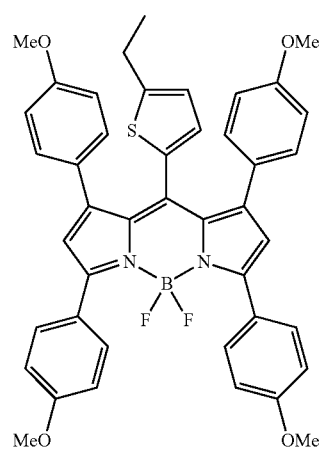
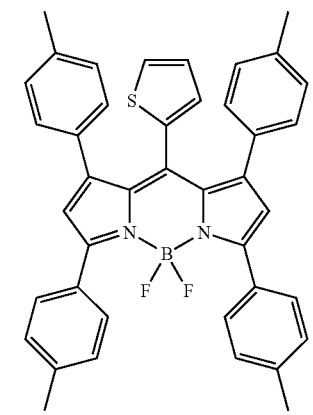
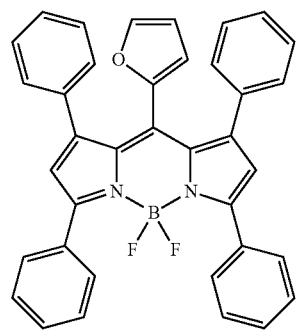
-continued
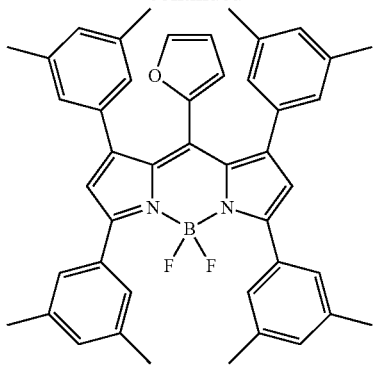
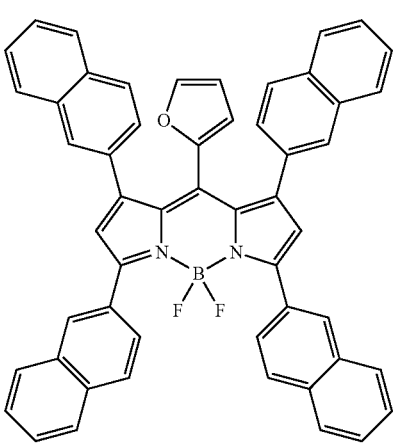
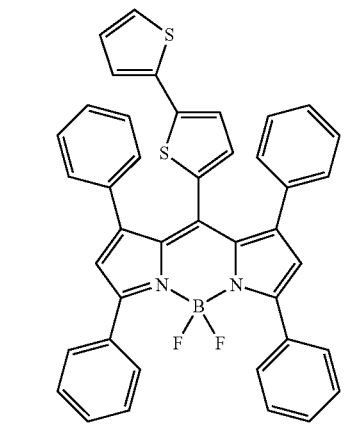
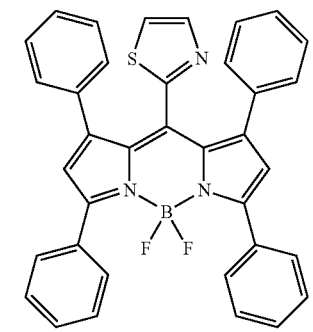

-continued
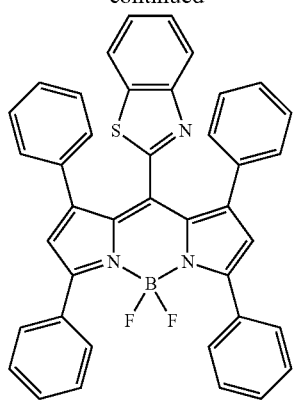
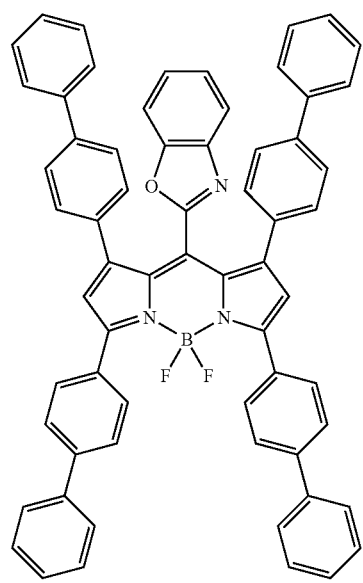
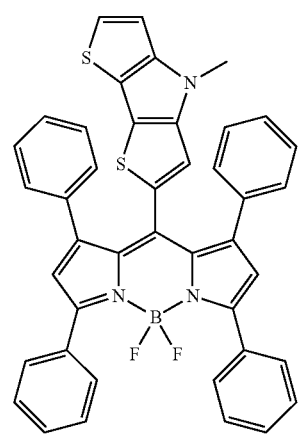
-continued
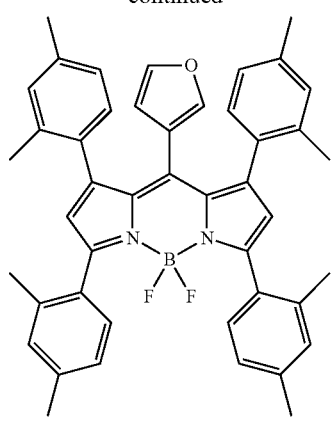
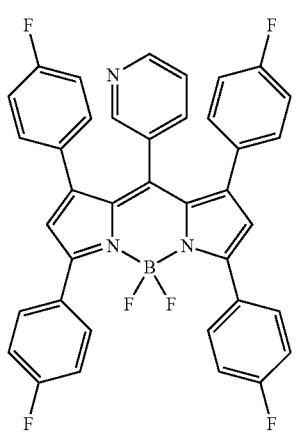
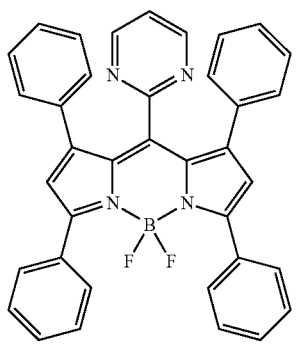
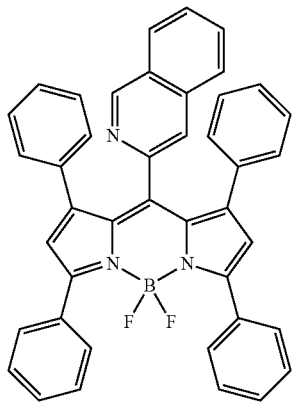

-continued
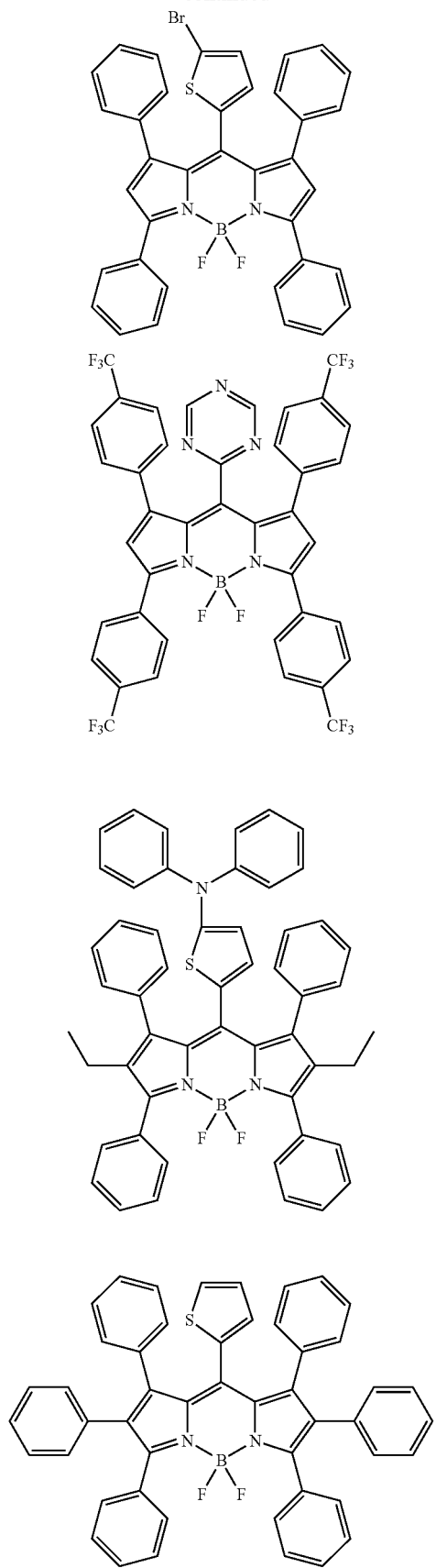
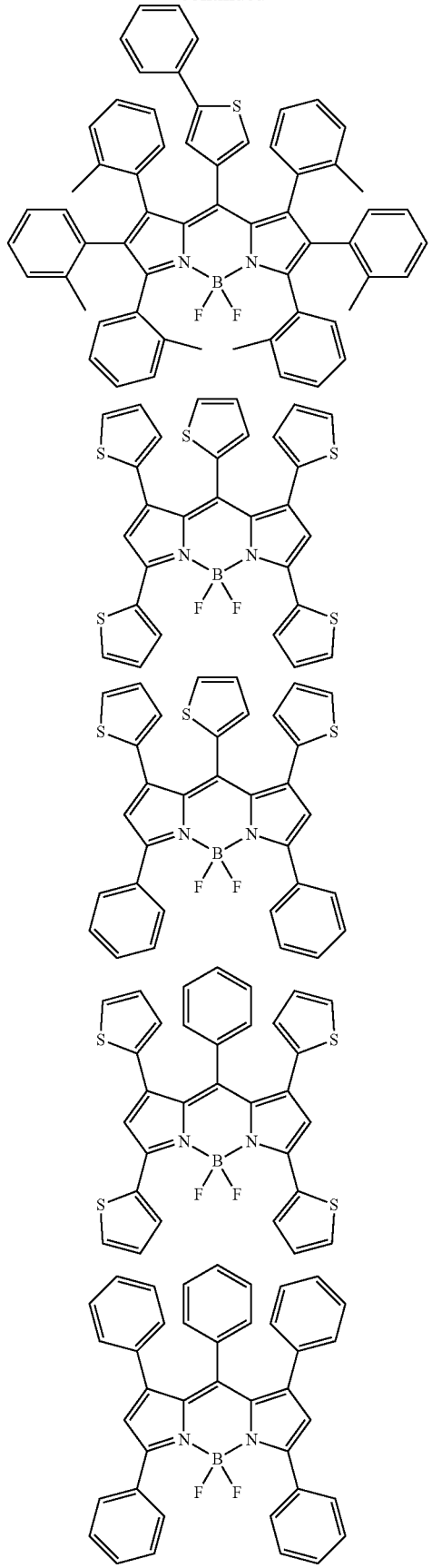

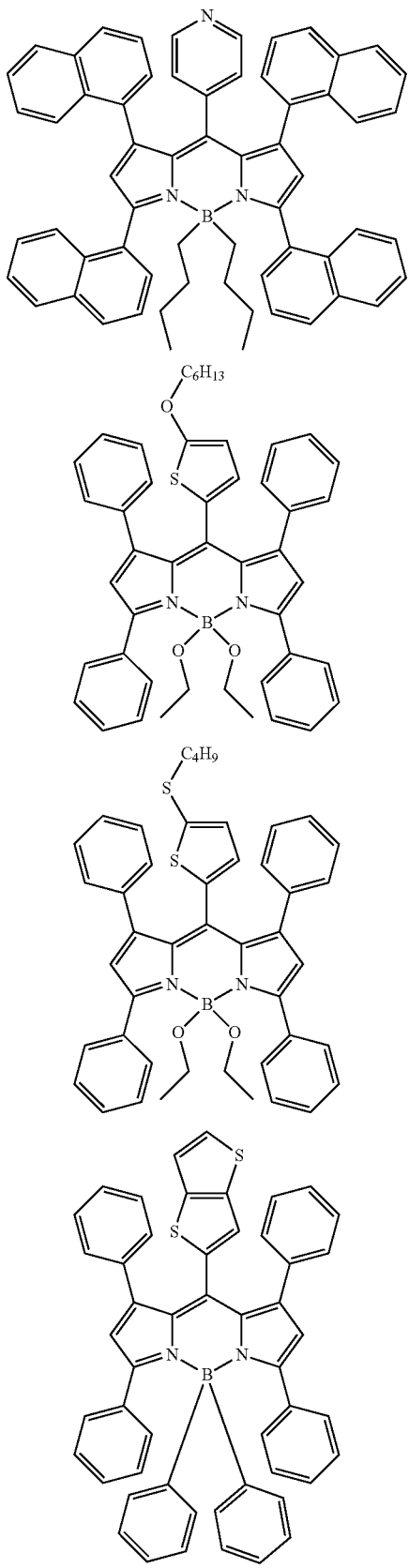
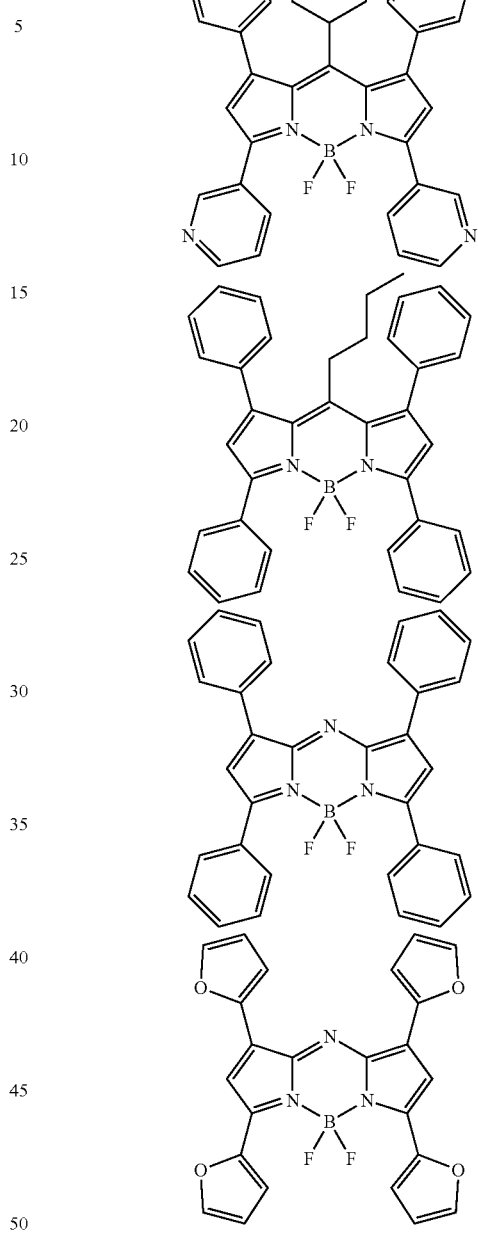

The molecular weight of the compound represented by General Formula (1) is preferably 200 to 1,500 and more preferably 300 to 900. In a case where the molecular weight of the compound is less than or equal to 1,500, the vapor deposition temperature does not increase, and therefore, decomposition of the compound hardly occurs. In a case where the molecular weight of the compound is greater than or equal to 200, the glass transition point of a vapor deposition does not decrease, and therefore, the heat resistance of the photoelectric conversion element hardly decreases.

The compound represented by General Formula (1) is particularly useful as a material for a photoelectric conversion film used for an imaging element, an optical sensor, or a photoelectric cell. In general, the compound represented by General Formula (1) functions as an organic p-type compound (organic p-type semiconductor) within the photoelectric conversion film. In addition, the compound represented by General Formula (1) can also be used as other applications such as a coloring material, a liquid crystal material, an organic semiconductor material, an organic light emitting element material, a charge transport material, a pharmaceutical material, and a fluorescent diagnostic drug material.

(Organic n-Type Compound)

The organic n-type compound (organic n-type semiconductor) is an acceptor organic semiconductor, and refers to as an organic compound which is mainly represented by an electron transporting organic compound and has a property of easily accepting electrons. More specifically, the organic n-type compound refers to an organic compound having a higher electron affinity in a case where two organic compounds are brought into contact with each other. Accordingly, any organic compound can be used as the organic n-type compound as long as the organic compound has an electron accepting property more than the compound represented by General Formula (1) to be used and exhibits n-type semiconductor characteristics.

Preferred examples thereof include a fullerene or a fullerene derivative, a condensed aromatic carbon ring compound (a naphthalene derivative, an anthracene derivative, a phenanthrene derivative, a tetracene derivative, a pyrene derivative, a perylene derivative, and a fluoranthene derivative), 5- to 7-membered heterocyclic compounds (for example, pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyrrolidine, pyrrolopyridine, thiadiazolopyridine, dibenzoazepine, tribenzoazepine, and oligothiophene (trithiophene)) which contain a nitrogen atom, an oxygen atom, or a sulfur atom, a polyarylene compound, a fluorene compound, a cyclopentadiene compound, a silyl compound, and a metal complex having a nitrogen-containing heterocyclic compound as a ligand.

The molecular weight of the organic n-type compound is not particularly limited, but is preferably 200 to 1,500 and more preferably 300 to 900 from the viewpoint in which the effect of the present invention is more excellent.

In a case of an embodiment shown in FIG. 3 to be described below, fullerenes selected from the group consisting of fullerene and fullerene derivatives are preferable as the above-described organic n-type compound. Fullerene represents fullerene $C_{60}$, fullerene $C_{70}$, fullerene $C_{76}$, fullerene $C_{78}$, fullerene $C_{80}$, fullerene $C_{82}$, fullerene $C_{84}$, fullerene $C_{90}$, fullerene $C_{96}$, fullerene $C_{240}$, fullerene $C_{540}$, and mixed fullerene. The fullerene derivatives represent compounds obtained by adding substituents to fullerenes. An alkyl group, an aryl group, or a heterocyclic group is preferable as the substituents. Compounds disclosed in JP2007-123707A are preferable as the fullerene derivatives.

On the other hand, in the case of the embodiment shown in FIG. 2, it is desirable that the organic n-type compound is colorless or has an absorption maximum wavelength and/or an absorption waveform close to the compound represented by General Formula (1), and it is desirable that the specific numerical value of the absorption maximum wavelength is less than or equal to 400 nm or 500 nm to 600 nm. Any compound can be used as long as the compound has the characteristics of the above-described organic n-type compound and is suitable for absorption, and examples thereof include compounds disclosed in [0016] to [0019] in US2013-0112947.

The photoelectric conversion film preferably forms a bulk hetero structure which is formed in a state in which the above-described compound represented by General Formula (1) and the organic n-type compound are mixed with each other. The bulk hetero structure is a layer in which the organic p-type compound and the organic n-type compound are mixed with each other and dispersed in the photoelectric conversion film, and can be formed through any one of a wet method and a dry method, but is preferably formed through a co-vapor deposition method. In a case where the photoelectric conversion film has a hetero junction structure, defects that a carrier diffusion length of the photoelectric conversion film is short are compensated, and therefore, it is possible to improve the photoelectric conversion efficiency of the photoelectric conversion film. The bulk hetero structure is described in detail in [0013] to [0014] of JP-2005-303266A.

In a case where the organic n-type compound is fullerenes, the content of the organic n-type compound to the total content of the compound represented by General Formula (1) and the organic n-type compound (=film thickness in terms of single layer of organic n-type compound/(film thickness in terms of single layer of compound represented by General Formula (1)+film thickness in terms of single layer of organic n-type compound)×100) is preferably greater than or equal to 50 volume %, more preferably greater than or equal to 55 volume %, and still more preferably greater than or equal to 65 volume % from the viewpoint of responsiveness of the photoelectric conversion element. The upper limit is not particularly limited, but the content of the organic n-type compound to the total content of the compound represented by General Formula (1) and the organic n-type compound is preferably less than or equal to 95 volume % and more preferably less than or equal to 90 volume %. In a case where the organic n-type compound is a compound other than fullerenes, the above-described content is preferably 20 volume % to 80 volume %, more preferably 30 volume % to 70 volume %, and still more preferably 40 volume % to 60 volume %.

The photoelectric conversion film containing the compound represented by General Formula (1) of the present invention and the organic n-type compound is non-luminescent film and has characteristics different from those of an organic electric field light emitting element (OLED). In a case where the non-luminescent film is a film of which the luminescence quantum efficiency is less than or equal to 1%, the luminescence quantum efficiency is more preferably less than or equal to 0.5% and still more preferably less than or equal to 0.1%.

(Film Forming Method)

The photoelectric conversion film can be formed mainly through a dry film formation method. Specific examples of the dry film formation method include physical vapor phase growth methods such as a vapor deposition method (particularly a vacuum vapor deposition method), a sputtering method, an ion plating method, and a molecular beam epitaxy (MBE) method, or chemical vapor deposition (CVD) methods such as plasma polymerization. The vacuum vapor deposition method is preferable. In a case where a film is formed through the vacuum vapor deposition method, it is possible to set the manufacturing conditions such as the vacuum degree and the vapor deposition temperature in accordance with a usual method.

The thickness of the photoelectric conversion film is preferably 10 nm to 1,000 nm, more preferably 50 nm to 800 nm, and still more preferably 100 nm to 500 nm. In a case where the thickness thereof is greater than or equal to 10 nm, a suitable dark current controlling effect is obtained. In a case where the thickness thereof is less than or equal to 1,000 nm, a suitable photoelectric conversion efficiency is obtained.

[Electrode]

The electrodes (the upper electrode (transparent conductive film) 15 and the lower electrode (conductive film) 11) are made of a conductive material. It is possible to use metal, alloy, a metal oxide, an electrically conductive compound, or a mixture thereof as the conductive material.

Since light is incident from the upper electrode 15, it is preferable that the upper electrode 15 is sufficiently transparent for light to be detected. Specific examples thereof include conductive metal oxides such as tin oxide (ATO, FTO) doped with antimony, fluorine, or the like, tin oxide, zinc oxide, indium oxide, indium tin oxide (ITO), and indium zinc oxide (IZO), metal thin films such as gold, silver, chromium, and nickel, mixtures or laminates of these metals and the conductive metal oxides, inorganic conductive substances such as copper iodide and copper sulfide, organic conductive materials such as polythiophene and polypyrrole, and laminates of the materials and ITO. Among them, transparent conductive metal oxides are preferable from the viewpoints of high conductivity and transparency, and the like.

In general, in a case where a conductive film is made to be thinner than a certain range, a resistance value is rapidly increased. In the solid-state imaging element into which the photoelectric conversion element according to the present embodiment is incorporated, the sheet resistance is preferably 100 to 10,000 Ω/□, and the degree of freedom of the range of the film thickness that can be thinned is large. In addition, as the thickness of the upper electrode (transparent conductive film) 15 is thinner, the amount of light absorbed becomes smaller and the light transmittance usually becomes larger. The increase in the light transmittance increases light absorbance in the photoelectric conversion film and increases the photoelectric conversion ability, which is significantly preferable. Considering control of leakage current, increase in a resistance value of the thin film, and increase in the transmittance accompanied by the thinning, the film thickness of the upper electrode 15 is preferably 5 to 100 nm and more preferably 5 to 20 nm.

There is a case where the lower electrode 11 has a transparency depending on the application or an opposite case where a material which does not have transparency and reflects light. Specific examples thereof include conductive metal oxides such as tin oxide (ATO, FTO) doped with antimony, fluorine, or the like, tin oxide, zinc oxide, indium oxide, indium tin oxide (ITO), and indium zinc oxide (IZO), metals such as gold, silver, chromium, nickel, titanium, tungsten, and aluminum, conductive compounds (for example, titanium nitride (TiN)) such as oxides or nitrides of these metals, mixtures or laminates of these metals and conductive metal oxides, inorganic conductive substances such as copper iodide and copper sulfide, organic conductive materials such as polyaniline, polythiophene, and polypyrrole, and laminates of the materials and ITO or titanium nitride.

The method for forming electrodes is not particularly limited, and can be appropriately selected in accordance with the electrode material. Specifically, electrodes can be formed through a printing method, a wet method such as a coating method, physical methods such as a vacuum vapor deposition method, a sputtering method, and an ion plating method, and chemical methods such as a CVD method and a plasma CVD method.

In a case where the material of the electrodes is ITO, it is possible to form the electrodes through an electron beam method, a sputtering method, a resistance thermal vapor deposition method, a chemical reaction method (such as a sol-gel method), and coating with a dispersion of indium tin oxide. Furthermore, it is possible to perform ultraviolet (UV)-ozone treatment, plasma treatment, and the like on a film manufactured using ITO. In a case where the material of the electrodes is TiN, various methods including a reactive sputtering method are used, and it is possible to further perform UV-ozone treatment, plasma treatment, and the like.

Charge Blocking Film: Electron Blocking Film, Hole Blocking Film]

The photoelectric conversion element of the present invention may have a charge blocking film. In the case where the photoelectric conversion element of the present invention has this film, the characteristics (such as photoelectric conversion efficiency or response speed) of photoelectric conversion element to be obtained become more excellent. Examples of the charge blocking film include an electron blocking film and a hole blocking film. Hereinafter, the films will be described in detail.

(Electron Blocking Film)

It is possible to use an electron donating organic material in an electron blocking film. Specifically, it is possible to use aromatic diamine compounds such as N,N'-bis(3-methylphenyl)-(1,1'-biphenyl)-4,4'-diamine (TPD) and 4,4'-bis[N-(naphthyl)-N-phenyl-amino]biphenyl (α-NPD), porphyrin compounds such as oxazole, oxadiazole, triazole, imidazole, imidazolone, a stilbene derivative, a pyrazoline derivative, tetrahydroimidazole, polyarylalkane, butadiene, 4,4',4"tris(N-(3-methylphenyl)-N-phenylamino) triphenylamine (m-MTDATA), phorphyrin, copper tetraphenylporphyrin, phthalocyanine, copper phthalocyanine, and titanium phthalocyanine oxide, a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, and a silazane derivative as a low molecular material. It is possible to use a polymer such as phenylenevinylene, fluorene, carbazole, indole, pyrene, pyrrole, picoline, thiophene, acetylene, and diacetylene, or a derivative thereof as a polymer material. It is also possible to use any compounds as long as they have sufficient hole transport ability without using the electron donating compounds. Specifically, compounds disclosed in [0083] to [0089] in JP2008-72090A, [0043] to [0063] in JP2011-176259A, [0121] to [0148] in JP2011-228614A, and [0108] to [0156] in JP2011-228615A are preferable.

The electron blocking film may be formed of a plurality of films.

It is possible to use an inorganic material as the electron blocking film. In general, an inorganic material has a dielectric constant larger than that of organic material. Therefore, in a case where the inorganic material is used in the electron blocking film, a large voltage is applied to the photoelectric conversion film, and therefore, it is possible to increase the photoelectric conversion efficiency. The material that can be used in the electron blocking film includes calcium oxide, chromium oxide, copper chromium oxide, manganese oxide, cobalt oxide, nickel oxide, copper oxide, copper gallium oxide, copper strontium oxide, niobium oxide, molybdenum oxide, copper indium oxide, silver indium oxide, and iridium oxide. In a case where the electron blocking film is formed of a single layer, it is possible to make the layer be made of an inorganic material. Alternately, in a case where the electron blocking film is formed of a plurality of layers, it is possible to make one or more layers be made of an inorganic material.

(Hole Blocking Film)

An electron accepting organic material can be used in a hole blocking film.

An oxadiazole derivative such as 1,3-bis(4-tert-butylphenyl-1,3,4-oxadiazolyl)phenylene (OXD-7), an anthraquinodimethane derivative, a diphenylquinone derivative, bathocuproine, bathophenanthroline, and derivatives thereof, a triazole compound, tris(8-hydroxyquinolinate)aluminum complex, bis(4-methyl-8-quinolinato)aluminum complex, distyrylarylene derivative, silole compound, and the like can be used as the electron accepting organic material. In addition, any material can be used as long as the material has sufficient electron transporting properties without using the electron accepting organic material. Porphyrin compounds, styryl compounds such as 4-dicyanomethylene-2-methyl-6-(4-(dimethylaminostyryl))-4H-pyran (DCM), and 4H-pyran compounds can be used. Specifically, compounds disclosed in [0073] to [0078] in JP2008-72090A are preferable.

A method for manufacturing the charge blocking film is not particularly limited, and a film can be formed through a dry film formation method or a wet film formation method. A vapor deposition method and a sputtering method can be used as the dry film formation method. Any one of the physical vapor deposition (PVD) and chemical vapor deposition (CVD) may be used for the vapor deposition, but physical vapor deposition such as vacuum vapor deposition is preferable. An inkjet method, a spray method, a nozzle printing method, a spin coating method, a dip coating method, a casting method, a die coating method, a roll coating method, a bar coating method, a gravure coating method, and the like can be used as the wet film formation method. The inkjet method is preferable from the viewpoint of high precision patterning.

The thickness of the charge blocking film (the electron blocking film and the hole blocking film) is preferably 10 to 200 nm, more preferably 30 to 150 nm, and still more preferably 50 to 100 nm. This is because, the effect of controlling dark current is deteriorated in a case where the thickness thereof is too thin, and the photoelectric conversion efficiency is deteriorated in a case where the thickness thereof is too thick.

[Substrate]

The photoelectric conversion element may further include a substrate. The type of substrate to be used is not particularly limited; and a semiconductor substrate, a glass substrate, and a plastic substrate can be used.

The position of the substrate is not particularly limited, but in general, a conductive film, a photoelectric conversion film, and a transparent conductive film are laminated on the substrate in this order.

[Sealing Layer]

The photoelectric conversion element may further include a sealing layer. In some cases, the performance of the photoelectric conversion material is significantly deteriorated due to the presence of deterioration factors such as water molecules. The deterioration can be prevented by sealing and coating the entirety of the photoelectric conversion film with a sealing layer such as diamond-like carbon (DLC) and ceramics such as metal oxide, metal nitride, and metal nitride oxide which are dense and into which water molecules do not permeate.

Selection of the material of the sealing layer and manufacture of the sealing layer may be performed in accordance with the disclosure in paragraphs [0210] to [0215] in JP2011-082508A.

[Optical Sensor]

Examples of the application of the photoelectric conversion element include a photoelectric cell and an optical sensor, but the photoelectric conversion element of the present invention is preferably used as an optical sensor. The above-described photoelectric conversion element alone may be used in an optical sensor. Alternately, a form of a line sensor in which photoelectric conversion elements described above are linearly arranged or a two-dimensional sensor in which the photoelectric conversion elements are arranged on a plane is preferable. In the line sensor, the photoelectric conversion element of the present invention functions as an imaging element by converting optical image information into an electric signal using a driving unit and an optical system such as a scanner. In the two-dimensional sensor, the photoelectric conversion element of the present invention functions as an imaging element by converting optical image information into an electric signal by imaging the optical image information on the sensor in an optical system such as an imaging module.

The photoelectric cell is a power generation device. Therefore, the efficiency of converting light energy into electric energy is an important performance. However, a dark current which is a current in a dark place does not cause a functional problem. Furthermore, a subsequent heating step such as a color filter installation is unnecessary. Conversion of a bright and dark signal into an electric signal with high accuracy is an important performance of the optical sensor. Therefore, the efficiency of converting the amount of light into a current is an important performance. However, since noise is generated in a case of outputting a signal in a dark place, a low dark current is required.

[Imaging Element]

Next, a configuration example of an imaging element including the photoelectric conversion element 10a will be described.

In the configuration example which will be described below, the same reference numerals or the corresponding reference numerals are attached to members or the like having the same configuration and action as those which have already been described, to simplify or not to repeat the description.

The imaging element is an element that converts optical information of an image into an electric signal, and is an element in which a plurality of photoelectric conversion elements are arranged on a matrix in the same plane, optical signals are converted into electric signals in each photoelectric conversion element (pixel), and it is possible to sequentially output the electric signals to the outside of the imaging elements for each pixel. For this reason, one pixel is formed of one photoelectric conversion element and one or more transistors.

Figure 3:
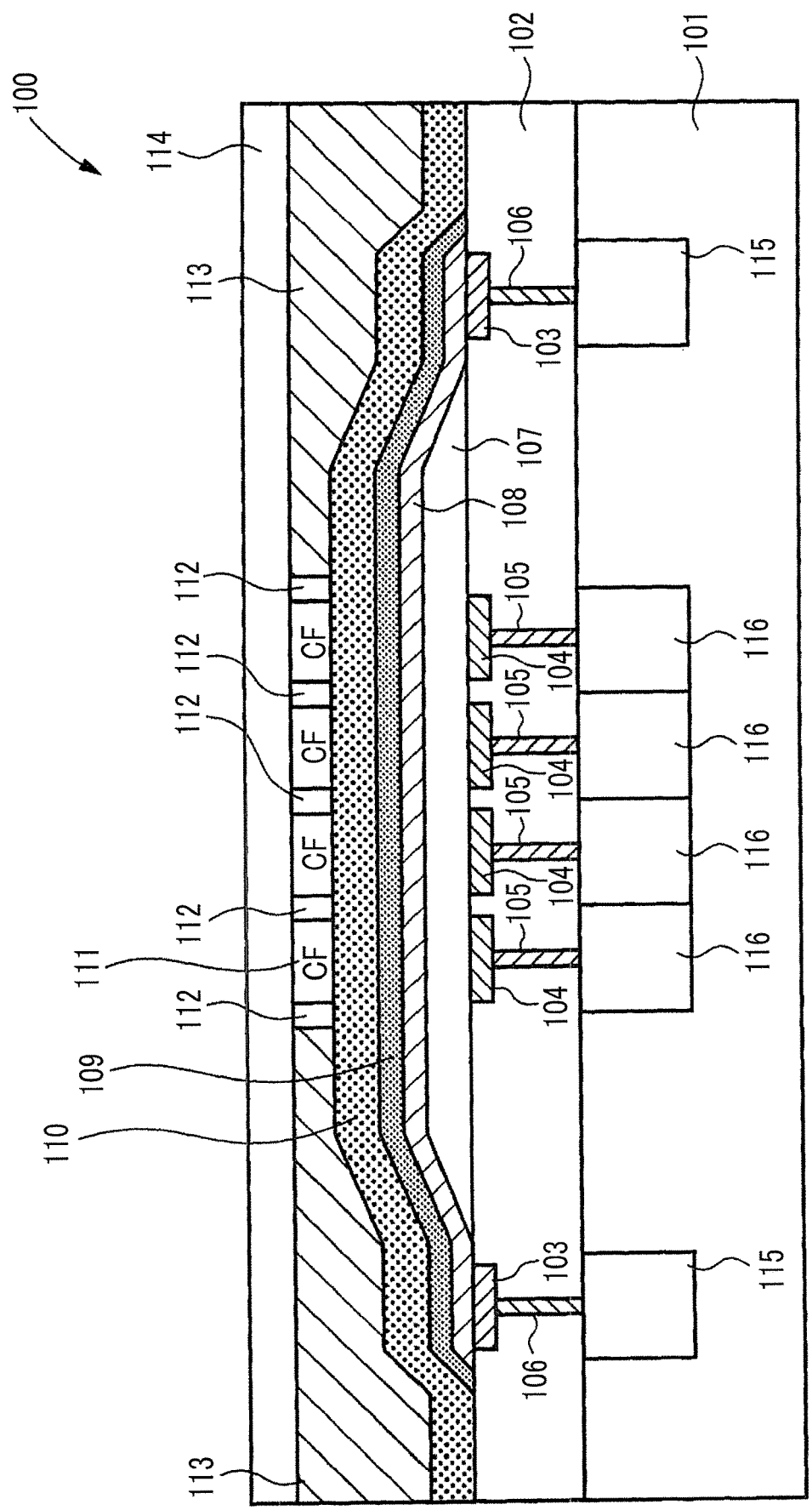
FIG. 3 is a schematic cross-sectional view of one pixel of an imaging element.

FIG. 3 is a schematic cross-sectional view showing a schematic configuration of an imaging element for describing an embodiment of the present invention. This imaging element is mounted on an imaging device such as a digital camera and a digital video camera, and imaging modules such as an electronic endoscope and a cellular phone.

The imaging element has a plurality of photoelectric conversion elements having configurations shown in FIGS.

1A and 1B and a circuit substrate in which a readout circuit reading out a signal corresponding to charges generated in a photoelectric conversion film of each photoelectric conversion element is formed. The imaging element has a configuration in which the plurality of photoelectric conversion elements are one-dimensionally or two-dimensionally arranged on the same surface above the circuit substrate.

An imaging element 100 shown in FIG. 3 includes a substrate 101, an insulating layer 102, connection electrodes 103, pixel electrodes (lower electrodes) 104, connection units 105, connection units 106, a photoelectric conversion film 107, a counter electrode (upper electrode) 108, a buffer layer 109, a sealing layer 110, a color filter (CF) 111, partition walls 112, a light shielding layer 113, a protective layer 114, a counter electrode voltage supply unit 115, and readout circuits 116.

The pixel electrodes 104 have the same function as that of the lower electrode 11 of the photoelectric conversion element 10a shown in FIG. 1A. The counter electrode 108 has the same function as that of the upper electrode 15 of the photoelectric conversion element 10a shown in FIG. 1A. The photoelectric conversion film 107 has the same configuration as that of the layer provided between the lower electrode 11 and the upper electrode 15 of the photoelectric conversion element 10a shown in FIG. 1A.

The substrate 101 is a glass substrate or a semiconductor substrate of Si or the like. The insulating layer 102 is formed on the substrate 101. A plurality of pixel electrodes 104 and a plurality of connection electrodes 103 are formed on the surface of the insulating layer 102.

The photoelectric conversion film 107 is a layer common to all the photoelectric conversion elements provided so as to cover the plurality of pixel electrodes 104.

The counter electrode 108 is an electrode common to all the photoelectric conversion elements provided on the photoelectric conversion film 107. The counter electrode 108 is formed on the connection electrodes 103 arranged on an outer side than the photoelectric conversion film 107, and is electrically connected to the connection electrodes 103.

The connection units 106 are buried in the insulating layer 102, and are plugs or the like for electrically connecting the connection electrodes 103 to the counter electrode voltage supply unit 115. The counter electrode voltage supply unit 115 is formed in the substrate 101 and applies a predetermined voltage to the counter electrode 108 via the connection units 106 and the connection electrodes 103. In a case where a voltage to be applied to the counter electrode 108 is higher than a power supply voltage of the imaging element, the power supply voltage is boosted by a boosting circuit such as a charge pump to supply the predetermined voltage.

The readout circuits 116 are provided on the substrate 101 corresponding to each of the plurality of pixel electrodes 104, and reads out a signal corresponding to charges trapped by the corresponding pixel electrodes 104. The readout circuits 116 are constituted, for example, of CCD and CMOS circuits or a thin film transistor (TFT) circuit, and are shielded by a light shielding layer not shown in the drawing which is disposed in the insulating layer 102. The readout circuits 116 are electrically connected to the corresponding the pixel electrodes 104 via the connection units 105.

The buffer layer 109 is formed on the counter electrode 108 so as to cover the counter electrode 108. The sealing layer 110 is formed on the buffer layer 109 so as to cover the buffer layer 109. Color filters 111 are formed on the sealing layer 110 at positions facing each of the pixel electrodes 104. The partition walls 112 are provided between the color filters 111 and are used for improving the light transmission efficiency of the color filters 111.

The light shielding layer 113 is formed on the sealing layer 110 in a region other than the region where the color filters 111 and the partition walls 112 are provided, and prevent light from entering the photoelectric conversion film 107 formed outside an effective pixel region. The protective layer 114 is formed on the color filters 111, the partition walls 112, and the light shielding layer 113, and protects the entirety of the imaging element 100.

In the imaging element 100 configured as described above, light which has entered is incident on the photoelectric conversion film 107, and charges are generated here. Holes among the generated charges are trapped by the pixel electrodes 104, and voltage signals corresponding to the amount are output to the outside of the imaging element 100 using the readout circuits 116.

A method for manufacturing the imaging element 100 is as follows.

The connection units 105 and 106, the plurality of connection electrodes 103, the plurality of pixel electrodes 104, and the insulating layer 102 are formed on the circuit substrate in which the counter electrode voltage supply unit 115 and the readout circuits 116 are formed. The plurality of pixel electrodes 104 are disposed, for example, in a square lattice shape on the surface of the insulating layer 102.

Next, the photoelectric conversion film 107 is formed on the plurality of pixel electrodes 104, for example, through a vacuum thermal vapor deposition method. Next, the counter electrode 108 is formed on the photoelectric conversion film 107 under vacuum, for example, through a sputtering method. Next, the buffer layer 109 and the sealing layer 110 are sequentially formed on the counter electrode 108, through the vacuum thermal vapor deposition method. Next, after forming the color filters 111, the partition walls 112, and the light shielding layer 113, the protective layer 114 is formed, and the imaging element 100 is completed.

Even in the method for manufacturing the imaging element 100, it is possible to prevent deterioration in performance of a plurality of photoelectric conversion elements by adding a step of placing the imaging element 100 which is in the middle of manufacture in a non-vacuum state, between the step of forming the photoelectric conversion film 107 and the step of forming the sealing layer 110. By adding this step, it is possible to control manufacturing cost while preventing the deterioration in performance of the imaging element 100.

EXAMPLES

Examples will be shown below, but the present invention is not limited thereto.

(Synthesis of Compound D-1)

A compound D-1 was synthesized according to the following scheme.

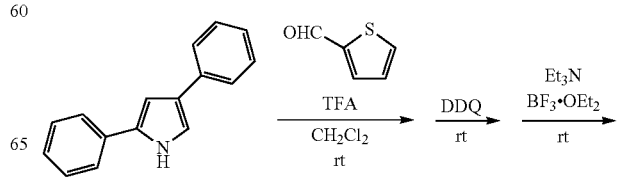

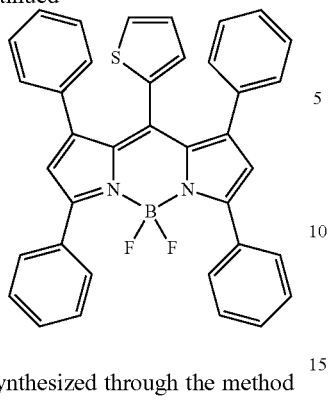

2,4-diphenylpyrrole was synthesized through the method disclosed in Chemistry A European Journal 2006, 12, 7254-7263. 2,4-diphenylpyrrole (2.19 g, 10 mmol) and 2-thiophene aldehyde (560 mg, 5.0 mmol) were added to methylene chloride (200 mL), and the obtained reaction solution was degassed through bubbling with nitrogen. Two droplets of trifluoroacetic acid (TFA) were added to the obtained reaction solution, and the mixture was stirred for 20 hours at room temperature. 2,3-dichloro-5,6-dicyano-p-benzoquinone (DDQ) (1.20 g, 5.3 mmol) was added to the obtained reaction solution, and the mixture was stirred for 5 hours at room temperature. Then, triethylamine (5.06 g, 50 mmol) was further added thereto, and the mixture was stirred for 5 minutes. Thereafter, boron trifluoride diethyl ether complex (8.63 g, 60 mmol) was added thereto, and the mixture was further stirred for 15 hours. Next, a saturated aqueous sodium hydrogen carbonate solution was added to the obtained reaction solution, extraction was carried out, and an organic phase was dried with magnesium sulfate, filtered, and concentrated to obtain a crude product. The obtained crude product was purified through silica gel column chromatography and recrystallized from methanol to obtain 492 mg (yield: 17%) of a compound (D-1). The obtained compound (D-1) was identified through nuclear magnetic resonance (NMR) and mass spectrometry (MS).

$^1$H NMR (400 MHz, CDCl$_3$): δ=6.10 (t, 1H), 6.55 (s, 2H), 6.56 (d, 1H), 6.72 (d, 1H), 6.9-7.1 (m, 10H), 7.4-7.5 (m, 6H), 7.8-7.9 (m, 4H). MS(ESI$^+$) m/z: 579.2 ([M+H]$^+$)

Hereinafter, synthesis of compounds (D-2) to (D-8) was performed using the same reaction.

A compound manufactured by Luminescence Technology was used as a compound (R-1) corresponding to a comparative compound. A compound (R-2) was synthesized according to a method disclosed in Chemistry Letters 2008, 37, 1094-1095.

D-1

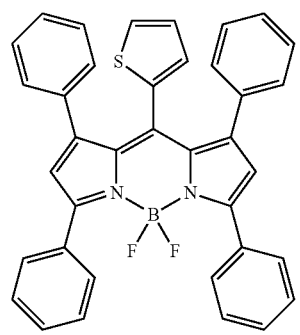

D-2

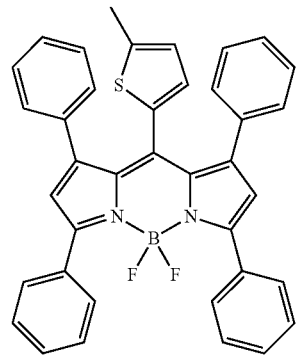

D-3

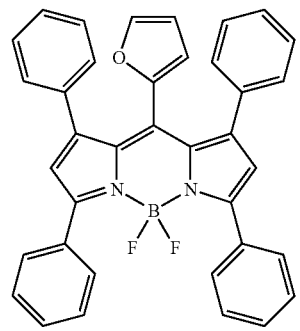

D-4

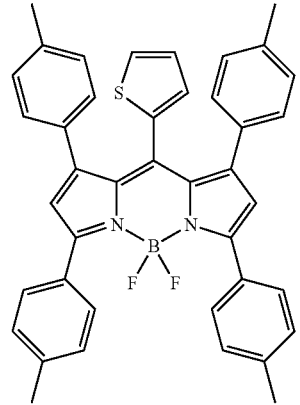

D-5

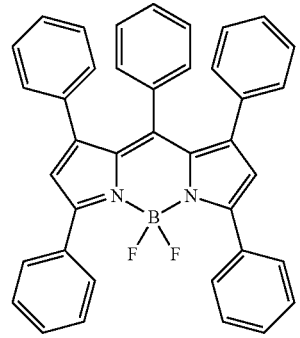

-continued

D-6
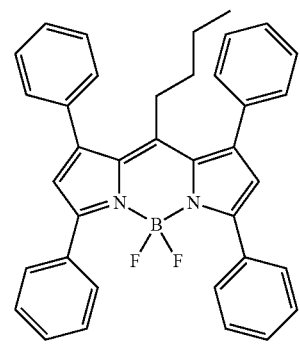

D-7
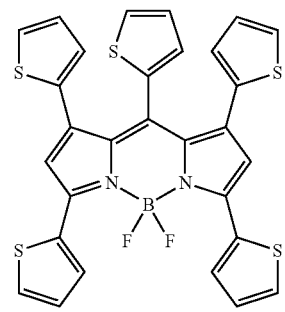

D-8
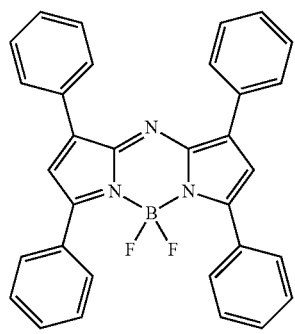

R-1
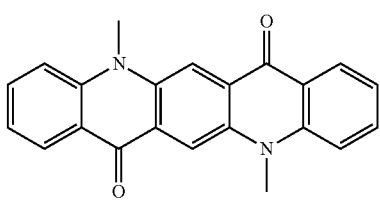

R-2
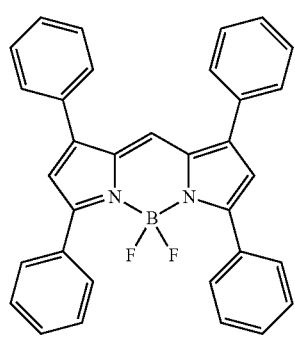

<Manufacture of Photoelectric Conversion Element>

A photoelectric conversion element in a form of FIG. 1A was manufactured using the obtained compounds. Here, the photoelectric conversion element includes a lower electrode 11, an electron blocking film 16A, a photoelectric conversion film 12, and an upper electrode 15.

Specifically, an amorphous ITO film was formed on a glass substrate through a sputtering method to form the lower electrode 11 (thickness: 30 nm), a molybdenum oxide ($MoO_x$) film was further formed on the lower electrode 11 through a vacuum thermal vapor deposition method to form a molybdenum oxide layer (thickness: 60 nm) as the electron blocking film 16A.

Furthermore, the compound (D-1) and the following compound (N-1) were subjected to co-vapor deposition through vacuum thermal vapor deposition so as to be respectively 50 nm in terms of a single layer so as to form a film on a molybdenum oxide layer in a state where the temperature of the substrate was controlled to be 25° C., and the photoelectric conversion film 12 having a bulk hetero structure of 100 nm was formed.

Furthermore, an amorphous ITO film was formed on the photoelectric conversion film 12 through a sputtering method to form the upper electrode 15 (transparent conductive film) (thickness: 10 nm). After forming a SiO film on the upper electrode 15 as a sealing layer through thermal vapor deposition, an aluminum oxide ($Al_2O_3$) layer was formed thereon through atomic layer chemical vapor deposition (ALCVD) method to manufacture a photoelectric conversion element.

N-1
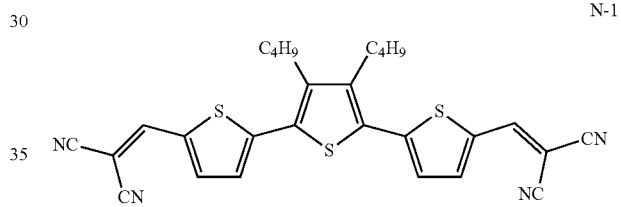

<Evaluation>
(Evaluation of Dark Current)

Evaluation of the following dark current was performed using the obtained photoelectric conversion element.

In the photoelectric conversion element of Example 1, an applied voltage in which the external quantum efficiency (the efficiency conversion of incident photons into output electrons) of photoelectric conversion at 550 nm in a bright place became 30% was first checked. Next, the same voltage was applied in a dark place, and the dark current value at that time was measured. The electric field strength at that time was $1\times10^5$ V/cm to $1\times10^6$ V/cm.

A photoelectric conversion element of each example and each comparative example was evaluated with a relative value while setting the dark current value of Example 1 as 1. The results are shown in Table 1.

The dark current of less than 1.5 was set to "A", the dark current of greater than or equal to 1.5 and less than 3 was set to "B", and the dark current of greater than or equal to 3 was set to "C". For practical use, "A" or "B" is preferable, and "A" is more preferable.

(Evaluation of Heat Resistance)

The following heat resistance was evaluated using each obtained photoelectric conversion element.

Each of the photoelectric conversion elements manufactured in a dark place was heated at 80° C. for 1 hour in a nitrogen atmosphere, and the dark current after heat treatment was measured. In the case of measuring the dark current, a test was performed by applying a voltage having the same value as that of each photoelectric conversion element applied during the above-described (Evaluation of Dark Current). The electric field strength at this time was $1\times10^5$ V/cm to $1\times10^6$ V/cm.

The photoelectric conversion element of each example and each comparative example was evaluated with a relative value of the dark current after heating while setting the dark current value before heating of each photoelectric conversion element as 1. The results are shown in Table 1. The relative value of the dark current after heating of less than 1.1 was set to "A", the relative value of greater than or equal to 1.1 and less than 1.5 was set to "B", and the relative value of greater than or equal to 1.5 and less than 3 was set to "C", and the relative value of greater than or equal to 3 was set to "D". For practical use, "A" or "B" is preferable, and "A" is more preferable.

Comparative Examples 1 and 2 after the film formation of the electron blocking material. Evaluation was also carried out in the same manner, and the same results as those in Table 1 were obtained. It was found that the imaging element was suitable for the manufacture and showed excellent performance.

EXPLANATION OF REFERENCES 10a, 10b: photoelectric conversion element
11: lower electrode (conductive film)
12: photoelectric conversion film
15: upper electrode (transparent conductive film)
16A: electron blocking film
16B: hole blocking film
100: pixel separation type imaging element

TABLE 1

| | Compound represented by General Formula (1) | | | | Other compounds | Evaluation | |
|---|---|---|---|---|---|---|---|
| | Type | $X^1$ | $R^3$ | $Ar^1$ to $Ar^4$ | | Dark current | Heat resistance |
| Example 1 | D-1 | $CR^3$ | Thienyl group | Aryl group | — | A | A |
| Example 2 | D-2 | $CR^3$ | Thienyl group | Aryl group | — | A | A |
| Example 3 | D-3 | $CR^3$ | Furyl group | Aryl group | — | B | A |
| Example 4 | D-4 | $CR^3$ | Thienyl group | Aryl group | — | A | A |
| Example 5 | D-5 | $CR^3$ | Phenyl group | Aryl group | — | B | B |
| Example 6 | D-6 | $CR^3$ | Butyl group | Aryl group | — | B | B |
| Example 7 | D-7 | $CR^3$ | Thienyl group | Heteroaryl group | — | A | B |
| Example 8 | D-8 | Nitrogen atom | — | Aryl group | — | B | B |
| Comparative Example 1 | — | — | — | — | R-1 | C | D |
| Comparative Example 2 | — | — | — | — | R-2 | C | C |

As shown in Table 1, it was confirmed that the photoelectric conversion elements of the present invention show excellent low dark current characteristics and heat resistance. Particularly, a small dark current at specific conversion efficiency is synonymous with an increase in S/N ratio, which is preferable as a photoelectric conversion element for an imaging element.

Among them, from the comparison between Examples 1 and 3, it was confirmed that a more excellent effect was obtained in a case where a sulfur atom was contained in $R^3$.

In addition, from the comparisons among Examples 1, 5, 6, and 8, it was confirmed that more excellent effect was obtained in the case of $CR^3$, of which $R^3$ was heteroaryl group, as $X^1$.

In addition, from the comparison between Examples 1 and 7, it was confirmed that more excellent effect was obtained in a case where $Ar^1$ to $Ar^4$ were aryl groups.

On the other hand, in Comparative Example 1 corresponding to an embodiment of Applied Physics Letters 2013, 103, 043305 and in Comparative Example 2 in which a predetermined compound not corresponding to the compound represented by General Formula (1) was used, it was confirmed that a desired effect was not obtained.

<Manufacture of Imaging Element>

The same imaging element as that shown in FIG. 3 was manufactured. That is, a 30 nm amorphous TiN film was formed on a CMOS substrate through a sputtering method, and was then used as a lower electrode through patterning such that each pixel was present on a photodiode (PD) on the CMOS substrate through photolithography. The imaging element was manufactured similarly to Examples 1 to 8 and 101: substrate
102: insulating layer
103: connection electrode
104: pixel electrode (lower electrode)
105: connection unit
106: connection unit
107: photoelectric conversion film
108: counter electrode (upper electrode)
109: buffer layer
110: sealing layer
111: color filter (CF)
112: partition wall
113: light shielding layer
114: protective layer
115: counter electrode voltage supply unit
116: readout circuit
200: photoelectric conversion element (hybrid type photoelectric conversion element)
201: inorganic photoelectric conversion film
202: n-type well
203: p-type well
204: n-type well
205 p-type silicon substrate
207: insulating layer
208: pixel electrode
209: organic photoelectric conversion film
210: common electrode
211: protective film
212: electron blocking film

What is claimed is:

1. A photoelectric conversion element having a conductive film, a photoelectric conversion film, and a transparent conductive film in this order, wherein the photoelectric conversion film contains a compound represented by General Formula (2) and an organic n-type compound,

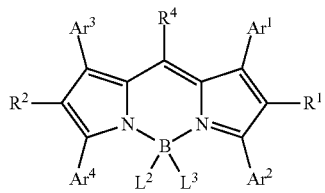

General Formula (2)

in General Formula (2), $Ar^1$ to $Ar^4$ each independently represent an aryl group or a heteroaryl group, $R^1$ and $R^2$ each independently represent a hydrogen atom or a substituent, $R^4$ represents a heteroaryl group, $L^2$ and $L^3$ each independently represent a type selected from the group consisting of a halogen atom, an alkyl group, an aryl group, a heteroaryl group, an alkoxy group, an aryloxy group, an alkylthio group, an arylthio group, a cyano group, and a nitro group.

2. The photoelectric conversion element according to claim 1,
wherein a hetero atom contained in the heteroaryl group represented by $R^4$ is a sulfur atom.

3. The photoelectric conversion element according to claim 1,
wherein $L^2$ and $L^3$ in General Formula (2) are both fluorine atoms.

4. The photoelectric conversion element according to claim 1,
wherein $Ar^1$ to $Ar^4$ in General Formula (2) are all aryl groups.

5. The photoelectric conversion element according to claim 1,
wherein the molecular weight of the organic n-type compound is 300 to 900.

6. The photoelectric conversion element according to claim 1,
wherein the photoelectric conversion film has a bulk hetero structure formed of the compound represented by General Formula (2) and the organic n-type compound.

7. An optical sensor comprising:
the photoelectric conversion element according to claim 1.

8. An imaging element comprising:
the photoelectric conversion element according to claim 1.

9. A compound represented by General Formula (3),

Y-Het¹   General Formula (3):

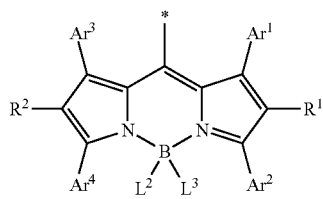

General Formula (4)

in General Formula (3), Y represents a mother nucleus represented by General Formula (4), $Het^1$ represents a heteroaryl group having only ring structures containing a hetero atom, the heteroaryl group has a monocyclic ring structure or is a group in which two or more ring structures containing a hetero atom are condensed, and the heteroaryl group contains an oxygen atom or a sulfur atom as a hetero atom, and in General Formula (4), $Ar^1$ to $Ar^4$ each independently represent an aryl group, $R^1$ and $R^2$ each independently represent a hydrogen atom or a substituent, $L^2$ and $L^3$ each independently represent a type selected from the group consisting of a halogen atom, an alkyl group, an aryl group, a heteroaryl group, an alkoxy group, an aryloxy group, an alkylthio group, an arylthio group, a cyano group, and a nitro group, and * represents a bonding position with $Het^1$.

10. The photoelectric conversion element according to claim 2,
wherein $L^2$ and $L^3$ in General Formula (2) are both fluorine atoms.

11. The photoelectric conversion element according to claim 2,
wherein $Ar^1$ to $Ar^4$ in General Formula (2) are all aryl groups.

12. The photoelectric conversion element according to claim 3,
wherein $Ar^1$ to $Ar^4$ in General Formula (2) are all aryl groups.

13. The photoelectric conversion element according to claim 2,
wherein the molecular weight of the organic n-type compound is 300 to 900.

14. The photoelectric conversion element according to claim 3,
wherein the molecular weight of the organic n-type compound is 300 to 900.

15. The photoelectric conversion element according to claim 4,
wherein the molecular weight of the organic n-type compound is 300 to 900.

16. The photoelectric conversion element according to claim 2,
wherein the photoelectric conversion film has a bulk hetero structure formed of the compound represented by General Formula (2) and the organic n-type compound.

17. The photoelectric conversion element according to claim 3,
wherein the photoelectric conversion film has a bulk hetero structure formed of the compound represented by General Formula (2) and the organic n-type compound.

18. The photoelectric conversion element according to claim 4, wherein the photoelectric conversion film has a bulk hetero structure formed of the compound represented by General Formula (2) and the organic n-type compound.

19. The photoelectric conversion element according to claim 5,
wherein the photoelectric conversion film has a bulk hetero structure formed of the compound represented by General Formula (2) and the organic n-type compound.

* * * * *